United States Patent [19]

Makovec et al.

[11] Patent Number: 4,826,878
[45] Date of Patent: May 2, 1989

[54] NEW DERIVATIVES OF 5-PENTYLAMINO-5-OXOPENTANOIC AND 4-PENTYLAMINO-4-OXOBUTANOIC ACIDS WITH ANTAGONISTIC ACTIVITY TOWARDS CHOLECYSTOKININ

[75] Inventors: Francesco Makovec; Rolando Chisté, both of Monza; Walter Peris, Milan; Luigi Rovati, Monza, all of Italy

[73] Assignee: Rotta Research Laboratorium S.p.A., Monza, Italy

[21] Appl. No.: 133,844

[22] Filed: Dec. 16, 1987

[30] Foreign Application Priority Data

Dec. 16, 1986 [IT] Italy ................................ 67937 A/86

[51] Int. Cl.$^4$ .......................................... C07C 101/42
[52] U.S. Cl. ................................... 514/561; 562/450; 549/57; 549/468; 548/492; 546/169; 514/443; 514/464; 514/419; 514/312
[58] Field of Search ................. 562/433, 450; 514/561

[56] References Cited

U.S. PATENT DOCUMENTS 4,439,617  3/1984  Sestanj et al. ...................... 562/450

OTHER PUBLICATIONS

Chemical Abstracts, vol. 103, No. 13, Abstract No. 99103r, Sep. 30, 1985.

*Primary Examiner*—Mary C. Lee
*Assistant Examiner*—Zinna Northington

*Attorney, Agent, or Firm*—Sughrue, Mion, Zinn, Macpeak, and Seas

[57] ABSTRACT

New original derivatives are described of 5-pentylamino-5-oxopentanoic and 4-pentylamino-4-oxobutasnoic acids having the formula:

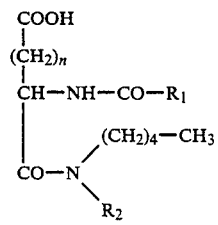

in which n is 1 or 2, $R_1$ is selected from the groups 2-naphthyl, 2 (or 3)-quinolinyl, 2 (or 3)-indolyl, 2 (or 3)-benzofuranyl, 2 (or 3)-benzothiophenyl, and $R_2$ is a pentyl group or an alkoxyalkyl group with 4 or 5 carbon atoms, preferably pentyl, 2-ethoxyethyl, 3-methoxypropyl or 3-ethoxypropyl.

The compounds have a powerful antagonistic activity towards cholecystokinin and are particularly useful in the treatment of illnesses of the digestive system, such as colitis, biliary diskinesia, pancreatitis or in the treatment of disorders of the central nervous system imputable to deficiencies in the physiological neuron levels of cholecystokinin or other related bioactive polypeptides.

6 Claims, No Drawings

NEW DERIVATIVES OF 5-PENTYLAMINO-5-OXOPENTANOIC AND 4-PENTYLAMINO-4-OXOBUTANOIC ACIDS WITH ANTAGONISTIC ACTIVITY TOWARDS CHOLECYSTOKININ

The subjects of the present invention are original derivatives of 5-pentylamino-5-oxopentanoic acid and 4-pentylamino-4-oxobutanoic acid which may be represented by the general formula shown below

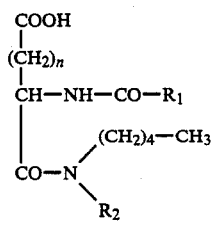
(I)

in which n is 1 or 2, $R_1$ is selected from the groups 2-naphthyl, 2 (or 3)-quinolinyl, 2 (or 3)-indolyl, 2 (or 3)-benzofuranyl, 2 (or 3)-benzothiophenyl, and $R_2$ is a pentyl group or an alkoxyalkyl group with 4 or 5 carbon atoms.

$R_2$ is preferably selected from the group consisting iof pentyl, 2-ethoxyethyl, 3-methoxypropyl and 3-ethoxypropyl.

The compounds which are the subject of the present invention show interesting pharmacological properties in mammals, which properties may be attributed to the powerful antagonistic activity towards cholecystokinin (CCK) or other bioregulatory peptides displayed by many of the subject compounds.

The compounds according to the invention may therefore be used to advantage in the treatment of various illnesses in man, such as illnesses of the digestive system, for example in the treatment of colitis, biliary diskinesia and pancreatitis.

On the basis of their pharmacological characteristics, their use may also be envisaged in the treatment of mental disorders imputable to deficiencies in the physiological neuron levels of CCK or other bioactive polypeptides and even in the treatment of anorexia.

The compounds which are the subject of the invention, as mentioned above, have a powerful anti-CCK activity in various experimental situations both in vivo and in vitro.

Thus, in nanomolar concentrations they inhibit the binding of marked cholecysstokinin to the cell membranes of ox gall-bladder, a tissue which is considered to be a target organ for the physiological action of cholecystokinin.

These compounds are, moreover, also very active in vivo. For example, they inhibit, in a dose-dependent manner, some even at doses lower than 1 mg/kg, the contraction and emptying of the gall-bladder induced by egg yolk which is an inducer for the endogenous release of CCK. They also encourage emptying of the stomach as they inhibit the pyloric contraction caused by CCK. Their protective action is, moreover, particularly powerful in experimental pancreatitis, for example in pancreatitis induced by sodium taurocholate.

Pharmaceutical forms of the compounds which are the subject of the invention may be prepared by conventional techniques, for exammple, as pills, capsules, suspensions, solutions and suppositories and may be administered orally, parentally or rectally.

The active ingredient is typically administered to the patient in a ratio of from 0.01 to 5 mg/kg of body weight per dose. For parenteral administration it is preferable to use a water-soluble salt of the subject compounds, such as the sodium salt or another salt which is non-toxic and pharmaceutically acceptable. As inactive ingredients, substances commonly used in the pharmaceutical industry may be used, such as excipients, binders, flavourings, dispersants, colourings, humectants, etc.

The method for the preparation of derivatives of 5-pentylamino-5-oxopentanoic acid and 4-pentylamino-4-oxobutanoic acid according to the invention is characterised in that it includes the steps of:

(a) reacting an internal anhydride of the formula:

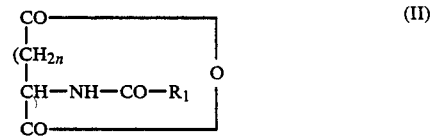
(II)

in which n and $R_1$ have the meanings attributed to them above, with an amine of formula

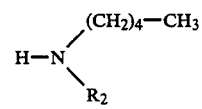

in which $R_2$ has the meaning attributed to it above, in a molar ratio of from 1 to 5 at a temperature of from $-10°$ C. to $10°$ C. and recovering the compounds of formula (I) from the reaction mass.

The internal anhydrides of formula II are new compounds which have not been synthesised before.

These internal anhydrides (II) are obtained by the steps of:

(b) reacting glutamic acid under Schotten-Bauman conditions with an equimolecular quantity of an acyl chloride of formula $R_1$—CO—Cl in which $R_1$ and n have the meanings attributed to then above, at a temperature of from $0°$ to $15°$ C. to obtain the N-acylated compound of formula:

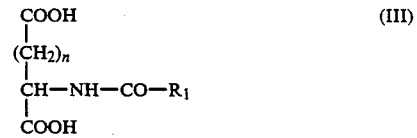
(III)

(c) dehydrating the compound of formula (III) by reaction in the presence of acetic anhydride in a molar ratio of from 1 to 10, alone or in the presence of an inert solvent miscible therewith, at a temperature of from $20°$ C. to the reflux temperature.

The series of steps constituting the method of the invention is shown as a whole in the following reaction scheme:

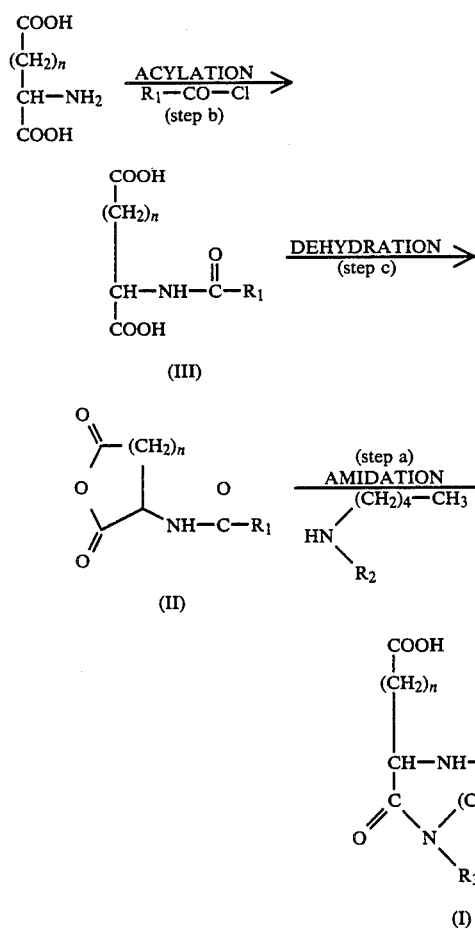

(III)

(II)

(I)

The acylation step b is carried out at a temperature of approximately 5° C. over a period of from 1 to 24 hours, preferably 12 hours.

In step c, the reaction time is typically approximately 30 minutes to 12 hours, preferably approximately 3 hours and the quantity of acetic anhydride is preferably 3 moles per mole of compound (III).

In the amidation step "a", the amine of formula

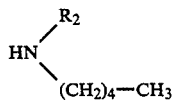

is preferably introduced in a molar ratio of 2.5 to 1 relative to the internal anhydride (II) and the reaction is carried out over a period of approximately 30 minutes to 12 hours, preferaly 3 hours.

The following examples are given in order better to illustrate the invention.

EXAMPLE 1

Preparation of 2-naphthoyl-glutamic acid (compound 1 of table 1)

100 ml of 1N sodium carbonate and 19.1 g (0.1 moles) of 2-naphthoyl chloride are added simultaneously with agitation and cooling to a solution containing 14.7 g (0.1 moles) of L-glutamic acid in 200 ml of 1N sodium carbonate cooled to 5° C. over a period of approximately 30 minutes.

The mixture is left to react for 12 hours. It is made acid to Congo red with concentrated HCl and the precipitate thus formed is filtered out. The precipitate is crystallised from $H_2O$-ethanol (2/1).

M.P.: 159°–61° C. TLC (isoamyl alcohol-acetone-$H_2O$: 5/2/2):

Rf 0.27. 26.5 g obtained. Yield 92%.

All the compounds of formula III are synthesised by the same method (see scheme above).

The compounds thus obtained are given in Table 1 below together with some of their identifying characteristics, the yields obtained and the crystallisation solvents used.

TABLE 1

N—acyl-glutamic and aspartic derivatives having the formula $$\begin{array}{c} COOH \\ | \\ (CH_2)_n \\ | \\ CH-NH-CO-R_1 \\ | \\ COOH \end{array}$$

| Compounds | n | $R_1$ | Melting point (°C.) | Solvents of crystallisation | % Yield |
|---|---|---|---|---|---|
| 1 | 2 | 2-naphthyl | 166–68 | Water-ethanol 2:1 | 92.0 |
| 2 | 2 | 2-indolyl | 142–44 | Water-ethanol 3:1 | 72.5 |
| 3 | 2 | 3-indolyl | 150–54 | Water-ethanol 3:1 | 73.0 |
| 4 | 2 | 2-quinolinyl | 98–104 | Ethyl acetate-ligroin | 55.0 |
| 5 | 2 | 2-benzofuranyl | 149–52 | Water | 73.1 |
| 6 | 2 | 3-benzofuranyl | 160–63 | Water | 78.0 |
| 7 | 2 | 2-benzothiophenyl | 158–61 | Water | 77.5 |
| 8 | 1 | 2-naphthyl | 174–76 | Water-ethanol 3:1 | 90.5 |
| 9 | 1 | 2-indolyl | 147–50 | Water-ethanol 3:1 | 74.5 |

EXAMPLE 2

Preparation of 2-naphthoyl-glutamic anhydride (compound 10 of Table 2)

30.6 g (0.3 moles) of acetic anhydride with 60 ml of isopropyl ether are added to 30.1 g (0.1 moles) of 2-naphthoyl glutamic acid. The mixture is heated under reflux (73°–77° C.) for 2 hours. It is cooled, filtered, washed with a little ether to remove residual acetic anhydride and dried. 24.8 g are thus obtained. Yield 88%.

M.P.: 181°–82° C.

All the compounds of formula II are synthesised by the same method (see scheme). Numerous examples of these compounds with some of their identifying characteristics, as well as the yields obtained, are given by way of example in Table 2 below.

TABLE 2

Derivatives of N—acyl-glutamic and aspartic anhydride having the formula

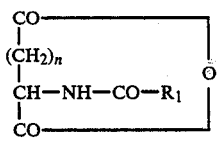

| Compounds | n | $R_1$ | Melting point (°C.) | % Yield |
|---|---|---|---|---|
| 10 | 2 | 2-naphthyl | 181–82 | 88 |
| 11 | 2 | 2-indolyl | 194–96 | 86 |
| 12 | 2 | 3-indolyl | 197–99 | 83 |
| 13 | 2 | 2-quinolinyl | 150–52 | 68 |
| 14 | 2 | 2-benzofuranyl | 176–78 | 84 |
| 15 | 2 | 3-benzofuranyl | 183–85 | 81 |
| 16 | 2 | 2-benzothiophenyl | 177–80 | 93 |
| 17 | 1 | 2-naphthyl | 201–03 | 90 |
| 18 | 1 | 2-indolyl | 195–97 | 85 |

EXAMPLE 3

Preparation of D,L-4-(2-naphthoylamino)-5-(di-n-pentylamino)-5-oxopentanoic acid (compound 19 of Table 3).

28.3 g (0.1 moles) of 2-naphthoyl-glutamic anhydride are placed in a reactor and suspended in 100 ml. of water. The suspension is cooled to approximately 5° and 39.3 g (0.25 moles) of di-n-pentylamine are added dropwise over a period of approximately 15 minutes. The mixture is left to react for 3 hours at this temperature and acidified with glacial acetic acid. It is filtered, washed with water until neutral and dried. 25.8 g are thus obtained. Yield 58.5%.

M.P. 119°–20° C. (crystallised from ethyl acetate). TLC:

Rf 0.95 (isoamyl alcohol-acetone-$H_2O$: 5/2/2).

All the compounds of formula I (see scheme) are synthesised by the same method.

Numerous examples of these compounds together with some of their identifying characteristics and the yields obtained are given in the table below.

TABLE 3

Derivatives having the formula

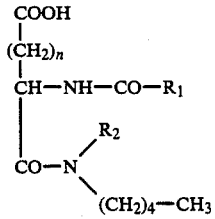

| Compounds | n | $R_1$ | $R_2$ | Melting point (°C.) | Solvents of Crystallisation | Rf* | Yield (%) | FORMULA |
|---|---|---|---|---|---|---|---|---|
| 19 | 2 | 2-naphthyl | pentyl | 119–20 | Ethyl acetate | 0.95 | 58.5 | $C_{26}H_{36}N_2O_4$ |
| 20 | 2 | 2-indolyl | pentyl | 190–92 | Ethyl acetate | 0.95 | 54.0 | $C_{24}H_{35}N_3O_4$ |
| 21 | 2 | 3-indolyl | pentyl | 197–99 | Ethyl acetate | 0.92 | 47.0 | $C_{24}H_{35}N_3O_4$ |
| 22 | 2 | 2-quinolinyl | pentyl | 81–4 | Iso-propyl ether | 0.89 | 24.0 | $C_{25}H_{35}N_3O_4$ |
| 23 | 2 | 2-benzofuranyl | pentyl | 117–18 | Ethyl acetate | 0.88 | 52.5 | $C_{24}H_{34}N_2O_5$ |
| 24 | 2 | 3-benzofuranyl | pentyl | 110–113 | Ethyl acetate | 0.85 | 51.0 | $C_{24}H_{34}N_2O_5$ |
| 25 | 2 | 2-benzothiophenyl | pentyl | 123–25 | Iso-propyl ether | 0.90 | 59.0 | $C_{24}H_{34}N_2O_4S$ |
| 26 | 1 | 2-naphthyl | pentyl | 133–35 | Ethyl acetate | 0.71 | 63.0 | $C_{25}H_{34}N_2O_4$ |
| 27 | 1 | 2-indolyl | pentyl | 195–98 | Ethyl acetate | 0.73 | 51.5 | $C_{23}H_{33}N_3O_4$ |
| 28 | 2 | 2-naphthyl | 3-metoxypropyl | 98–100 | Iso-propyl alcohol | 0.80 | 56.5 | $C_{25}H_{34}N_2O_5$ |
| 29 | 2 | 2-naphthyl | 2-ethoxyethyl | 110–12 | Iso-propyl alcohol | 0.82 | 44.0 | $C_{25}H_{34}N_2O_5$ |
| 30 | 2 | 2-naphthyl | 3-ethoxypropyl | 94–6 | Iso-propyl alcohol | 0.84 | 39.0 | $C_{26}H_{36}N_2O_5$ |
| 31 | 2 | 2-indolyl | 3-methoxypropyl | 167–70 | Iso-propyl alcohol | 0.83 | 52.0 | $C_{23}H_{33}N_3O_5$ |
| 32 | 2 | 2-benzofuranyl | 3-methoxypropyl | 85–7 | Iso-propyl ether | 0.79 | 44.5 | $C_{23}H_{32}N_2O_6$ |
| 33 | 1 | 2-naphthyl | 3-methoxypropyl | 106–09 | Iso-propyl alcohol | 0.68 | 56.0 | $C_{24}H_{32}N_2O_5$ |

*The values shown in the table relate to the eluent: isoamyl alcohol-acetone-water: 5/2/2

The powerful anti-cholecystokinin (anti-CCK) activity of the compounds of the invention will now bedocumented by a series of pharmacological experiments conducted both in vitro and in vivo.

Studies on binding to the cell membrane of ox gallbladders.

The capacity of some compounds of the invention to inhibit the binding of (125-I)-Bolton Hunter-CCK-8 to the cholecystokinin receptors of ox gallbladder membranes was evaluated by comparison with the displacement induced by cold (unmarked) CCK.

The ox gallbladder cell membranes were prepared by homogenisation with Tris buffer (pH 7.4) and centrifuging of the homogenate at 50,000 gravity for 10 minutes. The membranes were then incubated together with the radioactive tracer and the compounds under study for 2 h at 25° C.

After the supernatant liqud had been discarded, the radioactivity associated with the pellet was determined with a liquid scintillator. The specific binding was determined as the difference between the binding in the absence and in the presence of $10^{-6}M$ CCK-8.

The results obtained are given in Table 4 which shows the IC50 values, that is the concentration (in moles/liter) of the antagonist whichis able to displace 50% of the (125-I)-CCK-8 from the receptors.

| Compounds | IC50 (moles/liter) | Compounds | IC50 (moles/liter) |
|---|---|---|---|
| CCK-8 | $0.2 \times 10^{-9}$ | Compound 26 | $6.6 \times 10^{-9}$ |
| Compound 19 | $2.2 \times 10^{-9}$ | Compound 27 | $2.4 \times 10^{-8}$ |
| Compound 20 | $2.1 \times 10^{-8}$ | Compound 28 | $5.6 \times 10^{-9}$ |
| Compound 21 | $7.8 \times 10^{-8}$ | Compound 29 | $9.2 \times 10^{-9}$ |
| Compound 22 | $1.2 \times 10^{-7}$ | Compound 30 | $0.7 \times 10^{-8}$ |

-continued

| Compounds | IC50 (moles/liter) | Compounds | IC50 (moles/liter) |
|---|---|---|---|
| Compound 23 | $1.2 \times 10^{-8}$ | Compound 31 | $8.6 \times 10^{-8}$ |
| Compound 24 | $7.5 \times 10^{-8}$ | Compound 32 | $4.0 \times 10^{-8}$ |
| Compound 25 | $9.0 \times 10^{-8}$ | Compound 33 | $8.6 \times 10^{-9}$ |

From the data given in the table it can be seen that the claimed compounds antagonise the binding of CCK by 50% at concentrations which, for the most active compounds, are only 10–20 times greater than that of the specific antagonist, thus demonstrating a very high specificity of action.

In order to confirm the results of this study in vitro, some of the more active compounds were also tested in vivo.

Antispastic activity on the gallbladder in mice

Emptying of the gall bladder was induced by a single oral administration of 1 ml of a 30% suspension (weight/volume) of lyophilised egg yolk in a physiological solution.

As stated above once it has been absorbed egg yoke induces a release of endogenous CCK. This dose was selected as it causes practically complete emptying of the gallbladder.

The antagonistic compounds were administered intraperitoneally (i.p.) 15 minutes before the contractant.

The % antispastic activity for each dose was calculated from the following formula:

$$\% = \frac{P_1 - P_2}{P_3 - P_2} \times 100$$

where
$P_1$ = the average weight of the gallbladders of the group of animals treated with the drug plus the contractant.
$P_2$ = the average weight of the gallbladders of the group of animals treated with the contractant only.
$P_3$ = the average weigh of the gallbladders of the control group of animals.

The compounds were tested at various doses so as to enable the calculation of an ID50 value, that is the dose (in mg/kg i.p.) which is able to inhibit the contractant effect of the egg yolk by 50%.

The results obtained are given in Table 5 where the effects obtained are expressed as the ID50.

TABLE 5

| | antispastic activity on contraction of the gallbladder induced by egg yolk. | | |
|---|---|---|---|
| Compound | Doses (mg/kg i.p.) | % inhibition of the emptying of the gallbladder | ID50 (1) (mg/kg i.p.) |
| 19 | 0.03 | 12.1 | |
| | 0.1 | 41.2 | 0.11 |
| | 0.3 | 83.7 | (0.99) |
| 26 | 0.1 | 17.0 | |
| | 0.3 | 30.8 | 0.53 |
| | 1.0 | 66.7 | (0.97) |
| 28 | 0.1 | 16.5 | |
| | 0.3 | 36.2 | 0.62 |
| | 1.0 | 58.8 | (0.99) |
| ATROPINE | 5 | 3.7 | |
| | 10 | 21.6 | INACTIVE |
| | 15 | 10.5 | |
| PAPAVERINE | 25 | 0 | |
| | 50 | 0 | INACTIVE |

TABLE 5-continued

| | antispastic activity on contraction of the gallbladder induced by egg yolk. | | |
|---|---|---|---|
| Compound | Doses (mg/kg i.p.) | % inhibition of the emptying of the gallbladder | ID50 (1) (mg/kg i.p.) |
| | 75 | 26.1 | |

(1): r = the coefficient of correlation of the straight line of regression.

The emptying of the gallbladder is reduced by the compounds of the invention in a dose-dependent manner.

At a dose of 0.3 mg/kg the compound 19 almost completely blocks the contraction induced by the egg yolk.

Atropine, on the other hand, is inactive and papaverine is slightly active but only at the toxic dose of 75 mg/kg which causes the death of 20% of the animals treated.

Antispastic activity on pyloric contraction in rats

This experiment shows the contractant effect of CCK on the pyloric sphincter. A dose of 8 mcg/kg i.p. of CCK was used, which induced a sub-maximal contraction of the pylorus. The antagonistic compounds were administered (i.p.) 15 minutes before the contractant. 10 minutes after administration of the contractant the animals were treated per os with 25 ml/kg of H$_2$O. 5 minutes after the administration the animals were killed, their stomachs removed and the gastric content measured by removal with a syringe.

The % antispastic activity for each dose administered was calculated from the following formula:

$$\% = \frac{V_2 - V_1}{V_2 - V_3} \times 100$$

where
$V_1$ = the volume of gastric content of the group of animals treated with the drug plus the contractant.
$V_2$ = the volume of gastric content of the group of animals treated with the contractant only.
$V_3$ = the volume of gastric content of the control group of animals.

Various doses of the compounds were tested so as to enable the calculation of an ID50 value, that is the dose (in mg/kg i.p.) which is able to inhibit the contractant effect of CCK by 50%.

The results obtained are given in Table 6 where the effects obtained are expressed as the ID50.

TABLE 6

| | Antispastic activity on the pyloric contraction induced by CCK in rats. | | |
|---|---|---|---|
| Compound | Doses (mg/kg i.p.) | % inhibition of the pyloric contraction | ID50 (1) (mg/kg i.p.) |
| 19 | 0.01 | 17.3 | |
| | 0.03 | 28.7 | 0.05 |
| | 0.1 | 70.7 | |
| | 0.3 | 95.5 | (0.98) |
| 26 | 0.03 | 24.8 | |
| | 0.1 | 50.0 | 0.14 |
| | 0.3 | 57.7 | |
| | 1.0 | 78.9 | (0.98) |
| 28 | 0.03 | 12.5 | |
| | 0.1 | 29.2 | 0.30 |
| | 0.3 | 46.7 | |
| | 1.0 | 73.0 | (0.99) |

(1): in brackets r = coefficient of correlation of the straight line of regression.

The pyloric contraction caused by 8 mcg/kg of CCK-8 is 50% inhibited by some of the compounds of the invention at very low doses of between 50 and 300 mcg/kg, that is at doses only 6-37 times greater than that of the hormonal contractant.

Pancreatitis induced by sodium taurocholate

The method described by Aho et al. (Scandinavian J. Gastroenterology 15 (1980), 411-16) was followed.

Male rats weighing approximately 250 g were subjected to laparotomy and the pancreas exposed. 0.3 ml of a 6% solution of sodium taurocholate were injected directly into the pancreatic tissue.

The products under examination were administered intraperitoneally (i.p.) 30 minutes before the operation and 3 hours after the operation.

6 hours after the laparotomy, blood was taken from the retro-orbital plexus after anaesthesia with ether, the animals were killed and the pancreas was removed and weighed. The activity of the serum amylase was determined by the Ceska method (Clin. Chim. Acta 26 (1969), 437-444(/)

The compounds were tested at various doses so as to enable the calculation of an ID50 value, that is the dose (in mg/kg i.p.) which is able to inhibit the toxic effect of the sodium taurocholate by 50%, expressed both as a % inhibition of the increase in weight of the pancreas and as a % inhibition of the increase in serum amylase.

The results obtained with the compounds 19 and 28 are given in Table 7.

logical experiment are lacking for this pathological condition.

A favourable therapeutic use of many of the subject compounds can furthermore be envisaged in various forms of anorexia and also in the treatment of some pathological conditions of the CNS linked to deficiencies in the physiological neuron levels of CCK or other bioactive peptides.

What is claimed is:

1. Pharmaceutically active compounds of 5-pentylamino-5-oxopentanoic and 4-pentylamino-4-oxobutanoic acids having the formula:

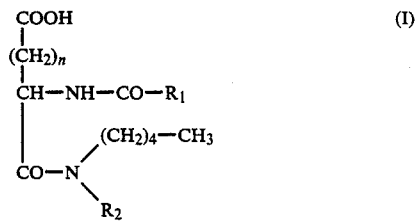

in which n is selected from 1 and 2, $R_1$ is 2-naphthyl, and $R_2$ is selected from the pentyl group and alkoxyalkyl groups having 4 or 5 carbon atoms, or a pharmaceutically-acceptable salt thereof.

2. A compound of claim 1, wherein $R_2$ is selected from the pentyl and 3-methoxypropyl groups.

TABLE 7

| | Examples of protective activity of the claimed compounds in experimental pancreatitis induced by taurocholate in rats. | | | |
|---|---|---|---|---|
| | % RATIO PANCREAS WEIGHT ANIMAL WEIGHT | % INHIBITION WEIGHT INCREASE (ID50 mg/kg ip) | AMYLASE IN THE SERUM (U/ml) | % INHIBITION AMYLASE INCREASE (ID50 mg/kg ip) |
| Controls | 0.39 | — | 8.0 | — |
| Controls + taurocholate | 0.54 | — | 16.6 | — |
| Compound 19 (1 mg/kg) + taurocholate | 0.49 | 33.3 | 12.7 | 45.3 |
| Compound 19 (3 mg/kg) + taurocholate | 0.43 | 73.3 | 10.0 | 76.7 |
| Compound 19 (10 mg/kg) + taurocholate | 0.40 ID50 = 1.7 | 93.3 (r = 0.98) | 8.8 ID50 = 1.1 | 90.7 (r = 0.98) |
| Controls | 0.35 | — | 7.7 | — |
| Controls + taurocholate | 0.59 | — | 13.7 | — |
| Compound 28 (3 mg/kg) + taurocholate | 0.52 | 29.2 | 11.0 | 45.0 |
| Compound 28 (10 mg/kg) + taurocholate | 0.47 | 50.0 | 9.6 | 68.3 |
| Compound 28 (20 mg/kg) + taurocholate | 0.43 ID50 = 9.2 | 66.6 (r = 0.99) | 8.4 ID50 = 4.1 | 88.3 (r = 0.99) |

(r) = coefficient of correlation

Sodium taurocholate induces pancreatitis which causes an increase in weight of the organ, which also becomes oedematous, lacking in elasticity and haemorrhagic.

The serum amylase, however, almost doubles.

These effects are blocked in a dose-dependent manner by the compounds of the invention. For example, compound 19 inhibits the weight increase of the pancreas and the serum amylase increase by 50% at a dose of approximately 1.5 mg/kg i.p.

The experimental data shown above have thus demonstrated the possible utility of these compounds in the treatment of various pathological conditions concerning the gastrointestinal tract, for example in spastic syndromes and pains generally, such as biliary diskinesia, or for encouraging emptying of the stomach and thus encouraging digestion.

These products could be used to particular advantage for the treatment of pancreatitis, as safely active drugs whose efficacy has been shown by pertinent pharmaco- 3. A pharmaceutical preparation comprising, a compound of claim 1 in an amount effective as an antispastic and an inert carrier.

4. A pharmaceutical preparation comprising a compound of claim 1 in an amount effective for the treatment of pancreatitis, and an inert carrier.

5. A pharmaceutical preparation comprising a compound of claim 1 in an amount effective for the treatment of pathological conditions of the CNS linked to deficiencies in the physiological neuron levels of cholecystokinin or other bioactive polypeptides, and an inert carrier.

6. A method for the treatment of spastic conditions, pancreatitis, pathological conditions of the CNS linked to deficiencies in the physiological neuron levels of cholecystokinin or other bio-active polypeptides in the human or animal body, the method comprising administering to said body an effective amount of a compound of claim 1.

* * * * *